(12) United States Patent
Allison et al.

(10) Patent No.: US 8,679,469 B2
(45) Date of Patent: Mar. 25, 2014

(54) GEL AIR FRESHENER

(75) Inventors: Gerald Allison, East Windsor, NJ (US); Nicholas O'Leary, Pennington, NJ (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/510,154

(22) PCT Filed: Dec. 2, 2010

(86) PCT No.: PCT/IB2010/055547
§ 371 (c)(1),
(2), (4) Date: May 16, 2012

(87) PCT Pub. No.: WO2011/067732
PCT Pub. Date: Jun. 9, 2011

(65) Prior Publication Data
US 2012/0219520 A1    Aug. 30, 2012

Related U.S. Application Data

(60) Provisional application No. 61/266,575, filed on Dec. 4, 2009.

(51) Int. Cl.
*A61L 9/04* (2006.01)

(52) U.S. Cl.
USPC .............................. 424/76.4; 512/4

(58) Field of Classification Search
USPC ............................. 424/76.4; 512/4
See application file for complete search history.

(56) References Cited

U.S. PATENT DOCUMENTS

| | | | |
|---|---|---|---|
| 5,780,527 A | 7/1998 | O'Leary | 523/102 |
| 6,960,625 B2 * | 11/2005 | Christenson et al. | 524/589 |
| 7,708,982 B2 | 5/2010 | O'Leary | 424/76.1 |
| 2002/0159961 A1 | 10/2002 | Yamato et al. | 424/65 |
| 2006/0078581 A1 | 4/2006 | Yamato | 424/401 |
| 2008/0015295 A1 * | 1/2008 | Williams et al. | 524/236 |
| 2009/0280076 A1 | 11/2009 | Yoshida et al. | 424/59 |
| 2012/0148965 A1 * | 6/2012 | Allison | 431/288 |

FOREIGN PATENT DOCUMENTS

| | | |
|---|---|---|
| WO | WO 96/05870 A1 | 2/1996 |
| WO | WO 97/26020 A1 | 7/1997 |
| WO | WO 00/24434 A1 | 5/2000 |
| WO | WO 03/102104 A1 | 12/2003 |
| WO | WO 2004/014438 A1 | 2/2004 |

OTHER PUBLICATIONS

International Search Report and Written Opinion, application No. PCT/IB2010/055547, mailed Mar. 3, 2011.

* cited by examiner

*Primary Examiner* — Aradhana Sasan
(74) *Attorney, Agent, or Firm* — Winston & Strawn LLP

(57) ABSTRACT

The present invention relates to the field of perfumery. It relates more particularly to a gel device which allows for an effective and prolonged evaporation of an active volatile ingredient. The gel device of the present invention includes an active volatile ingredient and a gelling agent of dibutyl lauroyl glutamide and dibutyl ethylhexanoyl glutamide.

14 Claims, No Drawings

GEL AIR FRESHENER

This application is a 371 filing of International Patent Application PCT/IB2010/055547, filed Dec. 2, 2010 and claims the benefit of U.S. application No. 61/266,575 filed Dec. 4, 2009.

TECHNICAL FIELD

The present invention relates to the field of perfumery. It relates more particularly to a gel device which allows for an effective and prolonged evaporation of an active volatile ingredient. The gel device of the present invention comprises an active volatile and a gelling agent comprising dibutyl lauroyl glutamide and dibutyl ethylhexanoyl glutamide.

PRIOR ART

The use of various devices for the diffusion of volatile compounds, for example perfumes, sanitizing agents, insect repellents and the like, has become more and more current in recent years. For example, air-freshening devices or deodorizers are currently used in practically all households to mask bad odors or to impart fragrances to the ambient air. The known devices used for the diffusion of volatile compounds into the surroundings make use of various principles. As an example, one can mention here dispersing devices of the spray type, aerosols or mechanical. Other examples include plastic packing elements enclosing the active ingredients in liquid form. Typically, the diffusion of the active ingredient takes place through membranes permeable to the vapors of said ingredient.

One class of systems capable of diffusing active volatile ingredients are solid state devices consisting of solid materials or carriers impregnated with an active ingredient. Such devices may be formed of various materials which are capable of absorbing the ingredient and subsequently releasing it in a more or less controlled manner. Examples of such known materials include gels, such as agar-agar or sodium stearate gels, synthetic polymer resins, or blocks of mineral material, e.g. plaster or silica.

It is particularly desirable to provide devices capable of diffusing active volatile ingredients which are efficient while maintaining good aesthetic properties. Particularly desired is a gel device capable of absorbing an amount of volatiles of up to 95% by weight or more, relative to the total weight of the gel. It would further be advantageous to provide gels capable of containing such high amounts of volatiles while being aesthetically pleasant, in particular being transparent. Improvement of the mechanical resistance of the gel is also constantly under investigation. Therefore, solid hard gels are desirable. In order to ensure a regular and prolonged activity of the gel, limiting exudation or syneresis of the volatiles out of the gel is also advantageous.

A few solutions to the above-mentioned problem have been proposed, but none is completely satisfactory.

In WO 00/24434 there is disclosed a solid gel composition containing up to 90% of perfume, a functionalised polymer such as a maleinised polybutadiene or polyisoprene, and a cross-linking agent of complementary functionality such as a polyoxyalkylenediamine.

However, said composition suffers from the drawback of imposing some limitations on the perfume formulation, as some perfuming ingredients such as esters, aldehydes and alcohols may react with the functionalised polymer and/or cross-linking agent and thus alter the fragrance of the perfume and the polymer's releasing properties. Moreover, the preparation and use of such a gel are such that it is preferable to associate the latter with a support, and therefore the amount of perfume, relative to the amount of carrier, is still limited.

Another perfuming device is known from WO 96/05870, wherein the gel is formed from different raw materials from those of the present invention. The gel there-described may contain up to 90% by weight of perfume. We have however found that the present invention can surprisingly incorporate slightly higher amounts of perfume, whilst using gelling agents that are advantageous from an environment point of view.

The gel disclosed in WO 2004/014438 is able to incorporate high amounts of active volatiles (i.e. up to 97.5%). However the gel disclosed in this document has the drawback of being formed less easily in the presence of hydroxyl derivatives, whereas the composition of the perfume is not subject to limitations in the gel devices of the present invention.

In WO 97/26020 there is mentioned the possibility of having a composition containing up to 95% of perfume, together with a polymer of the polyether-ester-amide type. However the methods of preparation of the composition which are described in said patent, i.e. the "drageoir" or the "master batch" methods, do not make it possible to obtain a uniform composition containing more than 55% of perfume, in spite of the inventors' claims. In fact we have ascertained that when the "drageoir" method, as disclosed in said patent application, and high quantities of perfume (e.g. more than 60%) are used, the polyether-ester-amide polymer is not able to entrap the totality of the perfume and thus the resulting products are mixtures of swollen resins soaking in the excess of perfume. The other manufacturing process disclosed in said application, namely the "master batch" method, which consists in the extrusion of the granules obtained by the "drageoir" method, allows even lower perfume loads. In other words, despite the claim that the known composition has up to 95% of perfume, the content of WO 97/26020 does not in fact allow a person skilled in the art to produce compositions containing more than 55% of perfume. Moreover, the compositions obtained according to WO 97/26020, unless containing small amounts of perfume, are not self-supporting and therefore require the use of particular packaging, limiting thus the possibility to reduce the amount of carrier.

Therefore, there is still a need for a composition which is transparent, solid, self-supporting, subject to minimal exudation and syneresis, capable of fully entrapping high quantities of active volatile ingredients and imposing a minimal constraint on the choice of the volatile composition to be used.

DETAILED DESCRIPTION OF THE INVENTION

The present inventors have solved the above mentioned problem by providing a gel device for the diffusion of a volatile active ingredient, comprising an oil containing a volatile active ingredient and a gelling agent containing dibutyl lauroyl glutamide and dibutyl ethylhexanoyl glutamide. Such device has the advantage of comprising solid gels containing up to 99% of perfume. It is also subject to minimal oil exudation and syneresis.

Advantageously, the gel device of the present invention can also be transparent.

The term "transparent" is used herein to connote a substantial absence of cloudiness or obscurity, so that the body of a device made of a "transparent" gel features an ability to let light pass through in a substantially unobstructed manner and has a high degree of clarity, with little or no cloudiness or haze. Decorative materials may be among the optional additives to the gels and devices of the present invention, which those skilled in the art would recognize as potentially obstructing light from passing through certain portions of the gels and devices. However, such gels or devices would nevertheless be included among those described as "transparent" herein, if the portions of the device or gel that do not contain such decorative materials would be otherwise considered transparent. Preferably, transparent gels or devices of the present invention have a degree of clarity, which is most preferably comparable to window glass, transparent glassware, or water. More preferably, the "transparent" gels or devices of the present invention have a transmittance of at least 80%, more preferably at least 85%, even more preferably at least 90% and most preferably at least 95%, as measured spectrophotometrically using water as a standard (100% transmittance) at 690 nm.

The gel contained in the device of the present invention is transparent, provided that it does not contain aliphatic esters, such as isopropyl myristate, or fatty acids, such as butyl stearate, in concentrations above 20%. Transparency is most important in devices wherein the gel is visible.

Dibutyl lauroyl glutamide and dibutyl ethylhexanoyl glutamide are both available commercially. For example, dibutyl lauroyl glutamide can be obtained under the trade-name GP-1 from Ajinomoto Co, Tokyo, Japan. Dibutyl ethylhexanoyl glutamide can be obtained from the same company, under the trade-name EB-21.

The gelling agent as a whole is typically present in an amount of from 1 to 10% by weight, preferably from 2 to 10% by weight, more preferably from 3 to 10% by weight, even more preferably from 4 to 6% by weight, relative to the total weight of the gel.

Dibutyl lauroyl glutamide and dibutyl ethylhexanoyl glutamide are preferably present in concentrations ranging from 0.5 to 5% each, preferably from 1 to 5% each, more preferably from 1 to 3% each, even more preferably from 2 to 3% each. The optimal concentrations ranges are between 1 and 3% of dibutyl lauroyl glutamide and between 2 and 3% of dibutyl ethylhexanoyl glutamide, and most preferably 3% of dibutyl lauroyl glutamide and 3% of dibutyl ethylhexanoyl glutamide. These percentages are defined by weight, relative to the total weight of the gel.

Lower concentrations of the two gelling agent than those above-cited can be used. This will change the properties of the gel. The concentrations of dibutyl lauroyl glutamide and dibutyl ethylhexanoyl glutamide may in particular be lower if they are used in combination with additional gelling agents, such as for example those described below.

In addition to the specific combination of dibutyl lauroyl glutamide and dibutyl ethylhexanoyl glutamide described above, the gelling agent may also contain additional components which are known to the skilled person as having a gelling effect. Examples of such optional additional components are N-acyl amino acid derivatives such as N-acyl amino acid amides and N-acyl amino acid esters prepared from glutamic acid, lysine, glutamine, aspartic acid and mixtures thereof. Non-limiting examples of N-acyl amino acid derivatives that may be used as optional additional gelling agents include N-lauroyl-glutamic acid diethyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof.

In a preferred embodiment of the invention, the gelling agent consists of dibutyl lauroyl glutamide and dibutyl ethylhexanoyl glutamide.

According to the invention, the gelling agent is combined with an oil which may be a hydrophobic active volatile ingredient as such, or a volatile ingredient dissolved in a suitable solvent. The total amount of the oil in the gel is preferably comprised between 70 and 99% by weight, more preferably between 80 and 97% by weight, even more preferably between 90 and 97% by weight and most preferably between 90 and 95% by weight, relative to the total weight of the gel. As a "volatile ingredient" it is meant here an individual ingredient, as well as a mixture of active volatiles ingredients.

The active volatile ingredient is preferably selected from a perfume, a malodor counteractant, a bactericide, an insecticide, an insect- or animal-repellent or attractant or a mixture thereof.

As "perfume" one may use any perfuming ingredient or a mixture thereof. A "perfuming ingredient" is meant here as a compound which is of current use in the perfumery industry, i.e. a compound which is used as active ingredient in perfuming compositions or in perfumed products in order to impart a hedonic effect into its surrounding. In other words, such an ingredient or mixture, to be considered as being a perfuming one, must be recognized by a person skilled in the art of perfumery as being able to impart or modify in a positive or pleasant way the odor of a composition or product, and not just as having an odor. Moreover, this definition is also meant to include compounds that do not necessarily have an odor but are capable of modulating the odor of a perfuming composition or of a perfumed product and, as a result, of modifying the perception by a user of the odor of such a composition or product.

The nature and type of these perfuming ingredients do not warrant a more detailed description here, which in any case would not be exhaustive, the skilled person being able to select them on the basis of his general knowledge, the intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils. Said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

By the term "malodor counteractant" or "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

Non-limiting examples of suitable insect repellants include citronella, dimethyl phthalate and n,n-dimethyl-m-tolumide.

Preferably, the active volatile is a perfume or a malodor counteractant. The gel device of the present invention is then preferably an air-freshener.

The active volatile can be dissolved in any suitable solvent. According to a preferred embodiment of the invention, the solvent is free of VOC compounds. By "VOC" we mean here the Volatile Organic Compounds as defined by the Environmental Protection Agency, and in particular we mean $C_1$-$C_5$ alkanols, such as ethanol, or $C_1$-$C_5$ alkanediols, such as ethylene glycol.

Examples of particularly appreciated VOC free solvents are methoxylated siloxanes (for example those sold under the Dow Corning® Fluid trade-names), mineral oils and vegetable oils such as for example olive oil, castor oil and sunflower oil.

Polar molecules such as fatty acids, fatty alcohols and glycols may optionally be added to the gel device of the present invention, in order to adjust the melting point and dissolution temperature of the gel. Indeed, these compounds are capable of lowering the melting point of the gel as desired, for technical and/or security reasons. The skilled person is able to select the types and amounts of such compounds on the basis of his general knowledge.

To prevent exudation, it is particularly appreciated to add 12-hydroxystearic acid, emollients such as ELDEW PS 203 (phytosteryl/octyldodecyl/lauroyl glutamate, origin Ajinomoto Co., Tokyo, Japan) and/or a thermoplastic polyamidic resin of polyether-ester-amide (such as those sold by ATO Chimie, Paris, France, under the trade-name Pebax®) as optional ingredient. Such optional ingredient, and in particular the thermoplastic polyamidic resin of polyether-ester-amide, is added in concentrations ranging from 0.5 to 5% by weight, more preferably from 2 to 5% by weight, relative to the total weight of the gel.

The gel device of the present invention may optionally include one or more additional components so to provide enhanced or additional aesthetic and/or functional improvements. In particular, the additional materials that may be included in the gel device include antibacterial agents, coloring agents, decorative materials, stabilizers, antioxidants, and UV blockers.

These optional ingredients do not warrant a more detailed description here, which would in any case not be exhaustive. The skilled person is capable to select them on the basis of his general knowledge and the desired characteristics of the gel device. In particular, the kind and amount of the additional ingredients are selected among those that do not alter the transparency of the gel that do not induce cloudiness or haze in the gel and do not alter its rigidity.

In a preferred embodiment of the invention, the gel consists of an oil and of a gelling agent consisting of dibutyl lauroyl glutamide and of dibutyl ethylhexanoyl glutamide.

The formed gels are characterized by a semi-solid to rigid gel structure

One of the principal advantages of the gels of the invention is their hardness. The gel is therefore preferably characterized by a needle penetration point measurement ranging from 50 to 250 mm, more preferably from 90 to 120 mm, even more preferably from 100 to 115 mm as measured using the ASTM D1321 method at 25° C.

The gel device of the present invention is also advantageous from an environment point of view. Indeed, as stated above, the solvent used in the invention can be VOC free. Moreover, the gelling agent is derived from amino acids and is not harmful to the environment. In particular, it is biodegradable. The gelling agent is also advantageous from a safety point of view with regard to the environment and human beings, so that it can even be used in cosmetic products.

We have also found that the gel device of the present invention advantageously provides a very uniform and prolonged diffusion of the active ingredient.

The gel device of the present invention contains the gel resulting of the admixture of the gelling agent with the oil. The device can consist of the gel as such.

In an alternative embodiment of the invention, the gel is coated on a surface or the surface is overdipped in the gel. By overdipping or coating, the gel is applied and adheres to the surface, so that the fragrance is then released from such surface. The surface preferably has limited inert surface area on which the free oil could be applied. Examples of suitable surfaces include sodium chloride crystals, rocks and botanical potpourri. The present gels have the advantage of adhering well to any of the surfaces and of having reduced exudation.

In another alternative, it can be in the form of a container containing the gel. Any type of container in which the gel can be contacted with the surrounding air is suitable for the purpose of the present invention. This alternative is the preferred form for the device of the present invention. In a particular embodiment, the container in which the gel is found is sealed, in order not to allow diffusion of the active ingredient into the surroundings. The customer will then activate the device simply by opening the container, after which the active ingredient will evaporate. This embodiment is possible because the gels obtained after mixing of the above-mentioned ingredients are perfectly stable for a period of several months and can hence be stored.

The invention also relates to a process for diffusing an active volatile ingredient into ambient air comprising exposing to air a gel device of the invention. In a preferred embodiment of the invention, the gel device is exposed to air in a closed space such as for example a room, a cupboard, a wardrobe or a drawer.

In another embodiment, the invention provides a process for the production of a gel device for the diffusion of an active volatile ingredient, wherein there is used a gelling agent containing dibutyl lauroyl glutamide and dibutyl ethylhexanoyl glutamide to form a gel with an oil containing the active volatile ingredient.

In a preferred embodiment, said process comprises
 a) heating an oil containing an active volatile ingredient to a temperature sufficient to solubilize the gelling agent of step b) into the oil; and
 b) adding to the heated oil a gelling agent containing dibutyl lauroyl glutamide and dibutyl ethylhexanoyl glutamide.

Preferably, the hydrocarbon oil is heated in step a) to a temperature comprised between 85 and 110° C.

In another preferred embodiment, said process further comprises the step of pouring the gel into a suitable container.

The optional ingredients that may be added to the gel device of the invention are typically added together with the oil in step a).

In the case of overdipping or coating of a surface, coating or overdipping is carried out using any method known in the art after mixing all the ingredients of the gel.

EXAMPLES

Example 1

Preparation of a Gel Device According to the Invention

A transparent gel device, Device A, was prepared by mixing the following ingredients in the amounts indicated.

TABLE 1

Composition of Device A

| Ingredient | Amount (%) |
| --- | --- |
| Perfume oil [1] | 95 |
| GP-1 [2] | 3 |
| EB-21 [3] | 2 |

[1] Perfume of the green floral type, origin: Firmenich SA, Geneva, Switzerland
[2] Dibutyl lauroyl glutamide, origin: Ajinomoto Co., Tokyo, Japan
[3] Dibutyl ethylhexanoyl glutamide, origin: Ajinomoto Co., Tokyo, Japan The perfume was heated to 85-90° C. in a vessel with closed lid. GP-1 and EB-21 were premixed and then added with mixing until the powder was completely dissolved. The mixture was then poured into an appropriate container and cooled to room temperature.

The physical properties of the gel were then determined. The needle penetration, as measured using the ASTM D1321 method at 25° C., was of 100 mm. A transmittance of 90% was measured with a ColorQuest XE spectrophotometer (origin: Hunter Lab) at 690 nm, using water as standard.

Example 2

Preparation of a Gel Device According to the Invention

A transparent VOC-free gel device, Device B, was prepared by mixing the following ingredients in the amounts indicated.

TABLE 2

Composition of Device B

| Ingredient | Amount (%) |
| --- | --- |
| Dow Corning ® [1] 245 | 50 |
| Perfume oil [2] | 45 |
| GP-1 [3] | 2 |
| EB-21 [4] | 3 |

[1] Decamethylcyclopentasiloxane, origin: Dow Corning Corporation, USA
[2] Perfume of the citrus floral type, origin: Firmenich SA, Geneva, Switzerland
[3] Dibutyl lauroyl glutamide, origin: Ajinomoto Co., Tokyo, Japan
[4] Dibutyl ethylhexanoyl glutamide, origin: Ajinomoto Co., Tokyo, Japan The perfume and Dow Corning® 245 were mixed and heated to 85-90° C. in a vessel with closed lid. GP-1 and EB-21 were premixed and then added with mixing until the powder was completely dissolved. The mixture was then poured into an appropriate container and cooled to room temperature.

The physical properties of the gel were then determined. The needle penetration, as measured using the ASTM D1321 method at 25° C., was of 115 mm. A transmittance of 90% was measured with a ColorQuest XE spectrophotometer (origin: Hunter Lab) at 690 nm, using water as standard.

Example 3

Preparation of a Gel Device According to the Invention

A transparent gel device, Device C, was prepared by mixing the following ingredients in the amounts indicated.

TABLE 3

Composition of Device C

| Ingredient | Amount (%) |
| --- | --- |
| Isopar ® M [1] | 80 |
| Perfume oil [2] | 15 |
| GP-1 [3] | 3 |
| EB-21 [4] | 2 |

[1] Isoparaffin, origin: Exxon Mobil Chemical, USA
[2] Perfume of the citrus floral type, origin: Firmenich SA, Geneva, Switzerland
[3] Dibutyl lauroyl glutamide, origin: Ajinomoto Co., Tokyo, Japan
[4] Dibutyl ethylhexanoyl glutamide, origin: Ajinomoto Co., Tokyo, Japan The perfume and Isopar® M were mixed and heated to 85-90° C. in a vessel with closed lid. GP-1 and EB-21 were premixed and then added with mixing until the powder was completely dissolved. The mixture was then poured into an appropriate container and cooled to room temperature.

The physical properties of the gel were then determined. The needle penetration, as measured using the ASTM D1321 method at 25° C., was of 110 mm. A transmittance of 95% was measured with a ColorQuest XE spectrophotometer (origin: Hunter Lab) at 690 nm, using water as standard.

Example 4

Preparation of a Gel Device According to the Invention

A transparent gel device, Device D, was prepared by mixing the following ingredients in the amounts indicated.

TABLE 4

Composition of Device D

| Ingredient | Amount (%) |
| --- | --- |
| Pebax ® 2533 SA 00 [1] | 3 |
| Perfume oil [2] | 92 |
| GP-1 [3] | 2 |
| EB-21 [4] | 3 |

[1] Thermoplastic polyamidic resin of polyether-ester-amide, origin: ATO Chimie, Paris, France
[2] Perfume of the fresh and clean ozone type, origin: Firmenich SA, Geneva, Switzerland
[3] Dibutyl lauroyl glutamide, origin: Ajinomoto Co., Tokyo, Japan
[4] Dibutyl ethylhexanoyl glutamide, origin: Ajinomoto Co., Tokyo, Japan The perfume and Pebax® 2533 SA 00 were mixed and heated to 85-90° C. in a vessel with closed lid. GP-1 and EB-21 were premixed and then added with mixing until the powder was completely dissolved. The mixture was then poured into an appropriate container and cooled to room temperature.

Example 5

Preparation of a Gel Device According to the Invention

A transparent gel device, Device E, was prepared by mixing the following ingredients in the amounts indicated.

TABLE 5

Composition of Device E

| Ingredient | Amount (%) |
| --- | --- |
| Pebax ® 2533 SA 00 [1] | 5 |
| Perfume oil [2] | 90 |

TABLE 5-continued

Composition of Device E

| Ingredient | Amount (%) |
|---|---|
| GP-1 [3] | 2 |
| EB-21 [4] | 3 |

[1] Thermoplastic polyamidic resin of polyether-ester-amide, origin: ATO Chimie, Paris, France
[2] Perfume of the fresh and clean ozone type, origin: Firmenich SA, Geneva, Switzerland
[3] Dibutyl lauroyl glutamide, origin: Ajinomoto Co., Tokyo, Japan
[4] Dibutyl ethylhexanoyl glutamide, origin: Ajinomoto Co., Tokyo, Japan The perfume and Pebax® 2533 SA 00 were mixed and heated to 85-90° C. in a vessel with closed lid. GP-1 and EB-21 were premixed and then added with mixing until the powder was completely dissolved. The mixture was then poured into an appropriate container and cooled to room temperature.

Example 6

Preparation of a Gel Device According to the Invention

A transparent gel device, Device F, was prepared by mixing the following ingredients in the amounts indicated.

TABLE 6

Composition of Device F

| Ingredient | Amount (%) |
|---|---|
| Perfume oil [1] | 99 |
| GP-1 [2] | 0.5 |
| EB-21 [3] | 0.5 |

[1] Perfume of the floral, musk, woody, sandalwood type, origin: Firmenich SA, Geneva, Switzerland
[2] Dibutyl lauroyl glutamide, origin: Ajinomoto Co., Tokyo, Japan
[3] Dibutyl ethylhexanoyl glutamide, origin: Ajinomoto Co., Tokyo, Japan The perfume was heated to 85-90° C. in a vessel with closed lid. GP-1 and EB-21 were premixed and then added with mixing until the powder was completely dissolved. The mixture was then poured into an appropriate container and cooled to room temperature.

What is claimed is:

1. A gel device for the diffusion of a volatile active ingredient comprising:
   a perfume oil containing an active volatile ingredient; and
   a gelling agent comprising dibutyl lauroyl glutamide and dibutyl ethylhexanoyl glutamide;
   wherein the active volatile ingredient is present in an amount of from 70 to 99% by weight, relative to the total weight of the gel device.

2. The gel device according to claim 1, wherein the gel is transparent and has a transmittance of at least 80%, as measured spectrophotometrically at 690 nm using water as standard.

3. The gel device according to claim 1 wherein the dibutyl lauroyl glutamide and dibutyl ethylhexanoyl glutamide, taken together, are present in an amount of from 3 to 10% by weight, relative to the total weight of the gel.

4. The gel device according to claim 1, wherein the oil further comprises a Volatile Organic Compounds (VOC)-free solvent.

5. The gel device according to claim 1, in the form of an air freshener.

6. The gel device according to claim 1, wherein the gel has a needle penetration point measurement of between 50 and 250 mm as measured using the ASTM D1321 method at 25° C.

7. The gel device according to claim 1, which consists of the recited oil and gelling agent.

8. A process for the production of a gel device according to claim 1, which comprises forming a gel with the perfume oil containing active volatile ingredient and with a gelling agent containing dibutyl lauroyl glutamide and dibutyl ethylhexanoyl glutamide.

9. The process according to claim 8, which comprises:
   heating the perfume oil containing active volatile ingredient to a temperature sufficient to solubilize the gelling agent into the oil; and
   adding to the heated oil the gelling agent of dibutyl lauroyl glutamide and dibutyl ethylhexanoyl glutamide to prepare a mixture that forms the gel.

10. The process according to claim 9, which further comprises pouring the mixture into a suitable container to form a gel having the shape of the container.

11. A process for diffusing an active volatile ingredient into ambient air, which comprises exposing to air the gel device of claim 1.

12. The process according to claim 11, wherein the gel device is exposed to air in a closed space.

13. A gel device for the diffusion of a volatile active ingredient consisting essentially of:
   a gelling agent comprising dibutyl lauroyl glutamide and dibutyl ethylhexanoyl glutamide which taken together, are present in an amount of from 3 to 10% by weight, relative to the total weight of the gel;
   a perfume oil containing an active volatile ingredient that is present in an amount of from 70 to 99% by weight, relative to the total weight of the gel device; and
   a Volatile Organic Compounds (VOC)-free solvent.

14. The gel device according to claim 13, wherein the gel is transparent and has a transmittance of at least 80%, as measured spectrophotometrically at 690 nm using water as standard, and has a needle penetration point measurement of between 50 and 250 mm as measured using the ASTM D1321 method at 25° C.

* * * * *